(12) United States Patent
Parish (10) Patent No.: US 9,423,324 B1
(45) Date of Patent: Aug. 23, 2016

(54) MACHINE FOR PREPARING AN ASPHALT SAMPLE BY POLISHING THE SURFACE OF THE SAMPLE AND ASSOCIATED METHOD

(71) Applicant: J.M. Parish Enterprises, LLC, Barberton, OH (US)

(72) Inventor: James M. Parish, Wadsworth, OH (US)

(73) Assignee: J.M. Parish Enterprises, LLC, Wadsworth, OH (US)

( * ) Notice: Subject to any disclaimer, the term of this patent is extended or adjusted under 35 U.S.C. 154(b) by 148 days.

(21) Appl. No.: 14/199,681

(22) Filed: Mar. 6, 2014

Related U.S. Application Data (60) Provisional application No. 61/773,876, filed on Mar. 7, 2013.

(51) Int. Cl.
*G01N 1/32* (2006.01)

(52) U.S. Cl.
CPC ...................... *G01N 1/32* (2013.01)

(58) Field of Classification Search
CPC ........ G01N 33/42; G01N 1/32; G01N 19/02; B24B 37/26
USPC .................. 73/863, 7, 8; 15/230.14, 230.16; 451/527, 288, 41, 550
See application file for complete search history.

(56) References Cited

U.S. PATENT DOCUMENTS

| | | | |
|---|---|---|---|
| 2,727,292 A * | 12/1955 | Houghton | F16L 33/04 24/279 |
| 2,949,908 A * | 8/1960 | McElroy | B24B 41/00 125/30.01 |
| 3,594,963 A * | 7/1971 | Beasley | B24B 13/01 29/421.1 |
| 3,699,721 A * | 10/1972 | Beasley | B24B 13/02 451/277 |
| 4,942,768 A | 7/1990 | McRae | |
| D314,325 S * | 2/1991 | Ziaylek, Jr. | D8/373 |
| 5,113,688 A | 5/1992 | Lazeration | |
| 5,275,056 A | 1/1994 | Hamilton et al. | |
| 5,659,140 A | 8/1997 | Jakob et al. | |
| 5,817,946 A | 10/1998 | Brovold | |
| 5,987,961 A | 11/1999 | Harris et al. | |
| 6,330,820 B1 * | 12/2001 | Cotterill | G01L 5/288 73/121 |

(Continued)

OTHER PUBLICATIONS

Robert Liang, Continuing Investigation of Polishing and Friction Characteristics of Limestone Aggregate in Ohio, 2009.*

(Continued)

*Primary Examiner* — Michael A Lyons
*Assistant Examiner* — David L Singer
(74) *Attorney, Agent, or Firm* — Renner, Kenner, Greive, Bobak, Taylor & Weber (57) ABSTRACT

A machine (10) for preparing a sample asphalt material (74) for testing includes a rotatable shaft (22) carrying a disc (28) adapted to engage the sample (74). A channel (26) which communicates with a source of water is formed in the shaft (22). A plate assembly (16) having a predetermined weight carries the shaft (22). An actuator assembly (18) moves the plate assembly (16) upwardly and releases the plate assembly (16) so that it is allowed to move downwardly so that the disc (28) contacts the sample (74) with only the weight of the plate assembly (16) being applied to the sample (74). The disc (28) is made of a rubber material and receives the water from the channel (26) through aperture (72) which communicates with slots (44) on the side of the disc (28) facing the sample (74). As a result, water is produced to the interface between the disc (28) and the sample (74) as the disc (28) rotates to polish the sample (74) and prepare it for testing.

9 Claims, 10 Drawing Sheets

(56) References Cited

U.S. PATENT DOCUMENTS

| | | | |
|---|---|---|---|
| 6,412,330 B1 | 7/2002 | Dicello et al. | |
| 6,925,889 B2 | 8/2005 | Pyle et al. | |
| 7,082,839 B2 | 8/2006 | Pyle et al. | |
| 7,614,275 B2 | 11/2009 | Lin et al. | |
| 7,632,170 B2* | 12/2009 | O'Moore | B24B 37/26 451/288 |
| 8,001,845 B2 | 8/2011 | Caulfield | |
| 2005/0274627 A1* | 12/2005 | Wylie | B24B 37/26 205/662 |
| 2008/0146129 A1* | 6/2008 | Kouzuma | B24B 37/24 451/527 |
| 2012/0253704 A1 | 10/2012 | Huang et al. | |

OTHER PUBLICATIONS

Robert Liang, 2007 Ohio Asphalt Paving Conference Pavement Friction Investigation.*

Robert Liang, Long Term Validation of an Accelerated Polishing Test Procedure for HMA Pavements, 2013.*

Robert Liang, Long Term Validation of an Accelerated Polishing Test Procedure for HMA Pavement, 2013.*

Accelerated Polishing Machine (VJ Tech—Building Better Technology, p. 91- undated).

The Development and Verification of a New Accelerated Polishing Machine (A Dissertation Presented to the Graduate Faculty of the University of Akron—by Mohammad Ali Khasawneh dated Aug. 2008, 251 pages total)—Part 1 of 3.

The Development and Verification of a New Accelerated Polishing Machine (A Dissertation Presented to the Graduate Faculty of the University of Akron—by Mohammad Ali Khasawneh dated Aug. 2008, 251 pages total)—Part 2 of 3.

The Development and Verification of a New Accelerated Polishing Machine (A Dissertation Presented to the Graduate Faculty of the University of Akron—by Mohammad Ali Khasawneh dated Aug. 2008, 251 pages total)—Part 3 of 3.

* cited by examiner

MACHINE FOR PREPARING AN ASPHALT SAMPLE BY POLISHING THE SURFACE OF THE SAMPLE AND ASSOCIATED METHOD

CROSS-REFERENCE TO RELATED APPLICATION

This application claims the benefit of U.S. Provisional Patent Application Ser. No. 61/773,876 filed Mar. 7, 2013, entitled Asphalt Testing System.

TECHNICAL FIELD

The present invention relates to a machine used to prepare an asphalt sample for testing. In particular, the present invention is directed to a machine used to prepare an asphalt sample for testing by polishing the surface of the asphalt sample. More particularly, the present invention is directed to an automated machine used to prepare an asphalt sample for testing by polishing the surface of the asphalt sample using a constant force on a rubber polishing disc that allows water to run through the disc to the sample.

BACKGROUND

An asphalt roadway is prone to losing its surface friction, or skid resistance, over time due to the traffic that utilizes the roadway. As the surface friction is reduced through the gradual wear that the tires impart on the asphalt, the ability of a vehicle to brake or maneuver is also reduced, thus leading to an increased chance of vehicular accidents.

In view of this, most roadways are now monitored to ensure that the roadways maintain adequate surface friction between the roadway surface and the tires of the vehicles using the roadways. This generally includes the use of the Locked Wheel Skid Trailer test to obtain skid number results. Based on this test, once the skid number falls below a threshold value, an action is taken to restore the surface friction to an adequate level. This can include resurfacing the roadway or reviving the surface in some other manner.

As there are costs involved with this monitoring and testing, tests and machines have been developed for testing an asphalt sample before using that particular type of asphalt on a roadway. Performing these tests before laying an asphalt material for a roadway ensures that the material will have properties that are ideal for that roadway.

Particular testing includes machines that attempt to anticipate how an asphalt material will wear over time. As different asphalt aggregates resist wear at different rates, these machines and tests have provided insight into the wear rates of the aggregates. This insight can then be used to determine the appropriate material to use on a particular roadway.

However, the known machines for preparing asphalt samples lack consistency and efficiency. Therefore, there is a need in the art for an improved machine for preparing asphalt samples for further testing.

SUMMARY OF THE INVENTION

It is thus an object of one aspect of the present invention to provide an apparatus for preparing a sample of asphalt material for testing which utilizes a rotating disc engaging the sample.

It is an object of another aspect of the invention to provide an apparatus, as above, in which water is applied to the interface between the disc and the sample to lubricate the sample and wash away abraded particles.

It is an object of a further aspect of the present invention to provide an apparatus, as above, with a disc having slots to spread the water over the surface of the sample.

It is an object of an additional aspect of the present invention to provide an apparatus, as above, which assures that a constant force is applied to the sample.

It is a still further object of the present invention to provide an apparatus, as above, which provides for the positive placement of the sample.

These and other objects of the present invention, as well as the advantages thereof over existing prior-art forms, which will become apparent from the description to follow, are accomplished by the improvements hereinafter described and claimed.

In general, an apparatus for preparing a sample asphalt material for testing includes a rotatable shaft carrying a disc which is adapted to engage the sample. A channel is formed in the shaft which communicates with a source of water. The disc has at least one slot therein communicating with water passing through the channel.

In accordance with another aspect of the invention, an apparatus used to prepare a sample asphalt material for testing includes a generally cylindrical body having a first surface and an opposed second surface. The second surface has at least one slot formed therein, the slot extending toward the first surface, and the first surface has at least one aperture communicating with the slot.

In another aspect of the present invention, an apparatus for maintaining a constant force of a disc on a sample asphalt material which prepares the sample for testing includes a plate assembly for moving a disc and having a desired predetermined weight, the disc being adapted to engage the sample. An actuator assembly can move the plate upwardly and releases the plate assembly so that it is allowed to move downwardly so that the disc contacts the sample with only the weight of the plate assembly thereby being applied to the sample.

An apparatus for preparing a sample asphalt material for testing according to these aspects includes a rotatable shaft which carries a disc that is adapted to engage the sample. A channel is formed in the shaft and communicates with a source of water. A plate assembly carries the rotatable shaft and has a predetermined weight. An actuator assembly moves the plate upwardly and releases the plate so that it is allowed to move downwardly so that the disc contacts the sample with only the weight of the plate assembly being applied to the sample. The disc has a generally cylindrical body having a first surface and an opposed second surface. The second surface has at least one slot formed therein which extends toward the first surface. The first surface has at least one aperture communicating with the slot. The slot and the aperture communicate with water passing through the channel.

The invention also includes a method of preparing a sample asphalt material for testing which includes the steps of contacting the sample with a disc with a predetermined force, rotating the disc against the surface of the sample, and providing water to the interface between the disc and the sample.

A preferred exemplary apparatus for preparing a sample asphalt material for testing is shown by way of example in the accompanying drawings without attempting to show all the various forms and modifications in which the invention might be embodied, the invention being measured by the appended claims and not by the details of the specification.

PREFERRED EMBODIMENT FOR CARRYING OUT THE INVENTION

Figure 1:
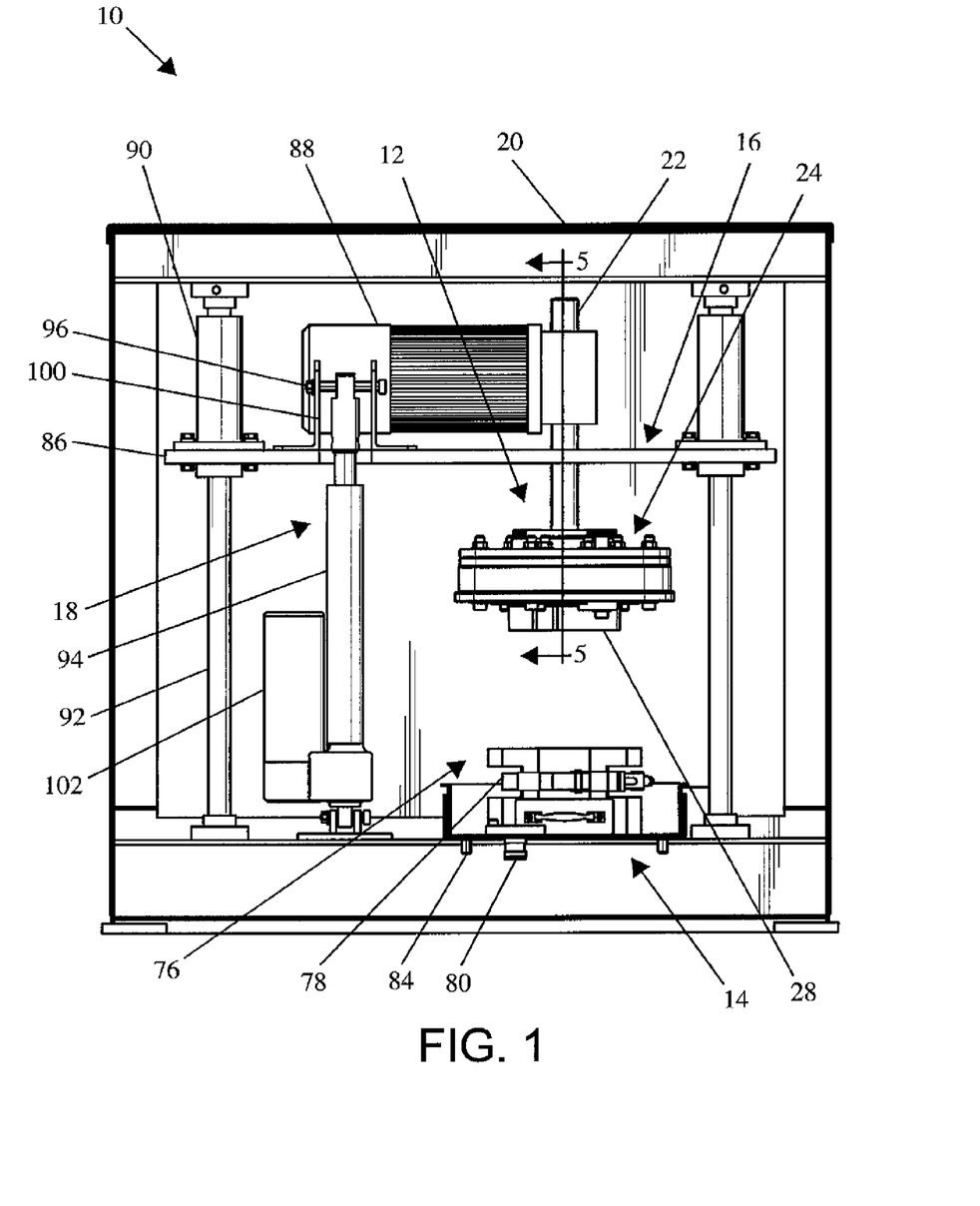
FIG. 1 is a somewhat schematic front elevational view of a machine for preparing asphalt samples made in accordance with the concepts of the present invention.
Figure 2:
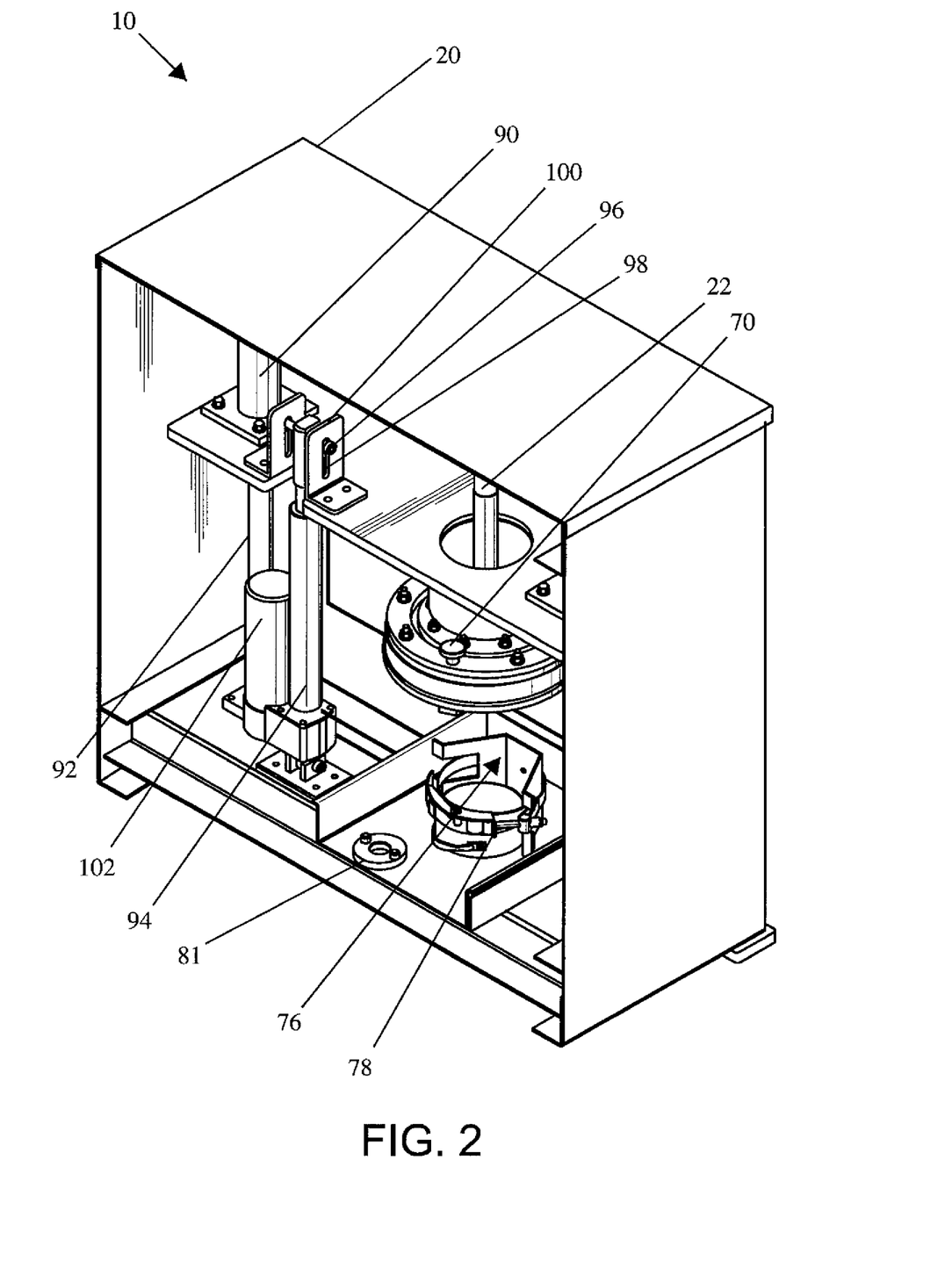
FIG. 2 is a perspective view of the machine shown in FIG. 1.

A machine for preparing asphalt samples for testing is generally indicated by the numeral 10 and includes a shaft assembly, generally indicated by the numeral 12, a sample assembly, generally indicated by the numeral 14, a plate assembly, generally indicated by the numeral 16, and an actuator assembly, generally indicated by the numeral 18, all positioned in a housing 20.

Shaft assembly 12 includes a shaft 22 which is rotated by a motor 88 and a disc assembly, generally indicated by the numeral 24, which includes a disc 28. Shaft 22 is provided with a hollow channel 26 that allows water to be passed through the shaft 22, as will hereinafter be described. Shaft 22 carries disc assembly 24 at its lower end and is coupled to the motor 88 at or near its upper end.

Figure 5:
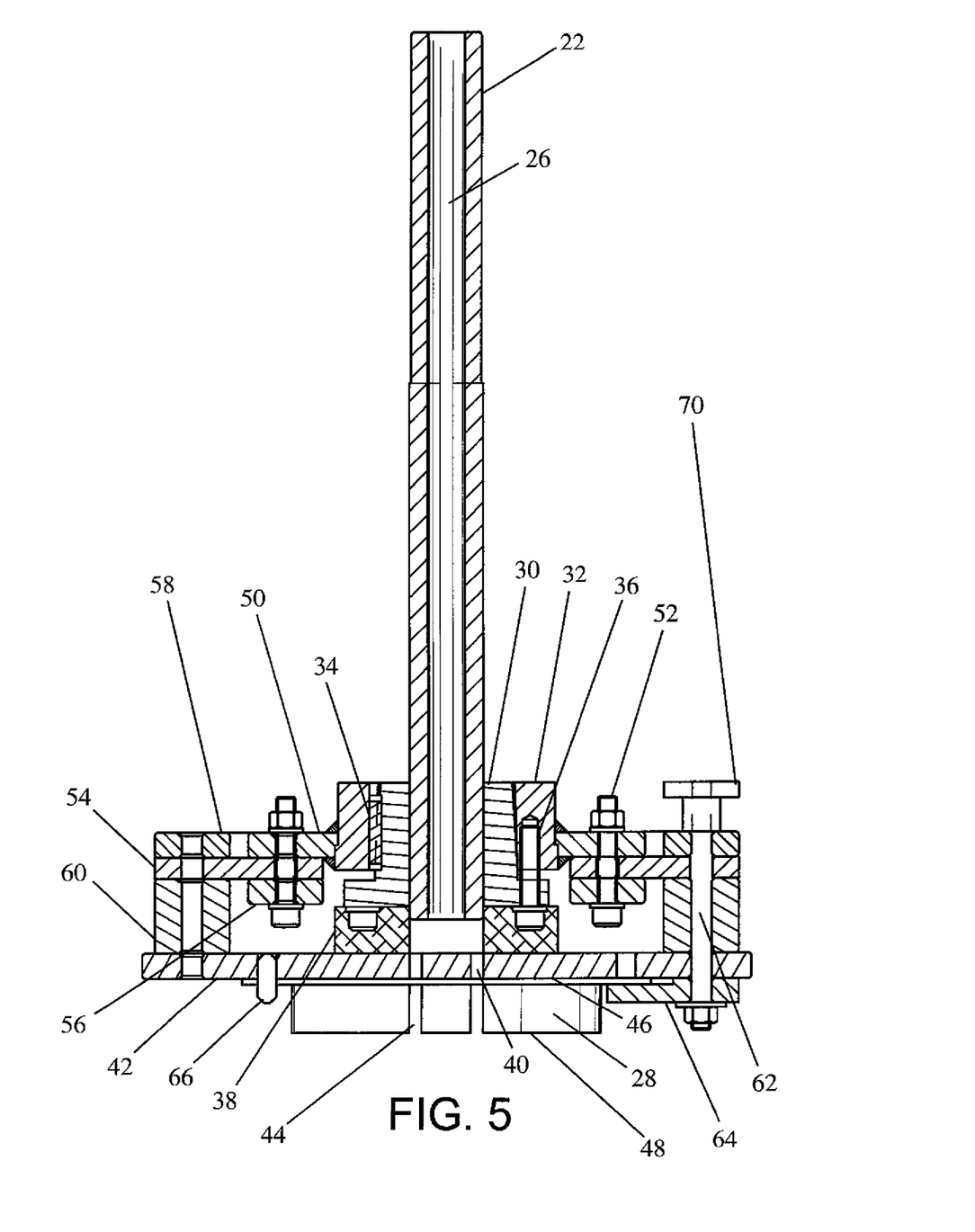
FIG. 5 is a sectional view of a hollow shaft carrying the mounting plate and a rubber disc taken substantially along line 5-5 of FIG. 1.

The manner in which shaft 22 carries disc assembly 24 is best seen in FIG. 5. Shaft 22 carries a tapered bushing 30 which is coupled to a hub 32 via a key 34. The tapered bushing 30 is further coupled to hub 32 via bolts 36. Water is provided from a suitable source to the top of channel 26 and flows, such as by gravity flow, through channel 26, through holes 40 in a mounting plate 42, through at least one aperture 72 in a first surface 46 of the disc 28, through at least one slot 44 provided through the second surface 48 of the disc 28, and to a top surface of a sample 74. A water seal 38 is provided to assure that the water is directed from channel 26 to disc 28.

Hub 32 is coupled, as by welding, to a drive plate 50. Bolts 52 couple the drive plate 50 to a rubber coupling 54 and an inner clamp ring 56. Rubber coupling 54 extends outwardly in order to couple the central components with the outward components of disc assembly 24. The rubber coupling 54 is sandwiched between an outer clamp ring 58 and a spacer 60 via bolts 62. Bolts 62 also couple the mounting plate 42 to the spacer 60. The rubber coupling 54 gives slight flexibility to disc assembly 24, for the purpose of allowing the disc 28 to align with a sample having a slightly unlevel top surface.

Figure 3:
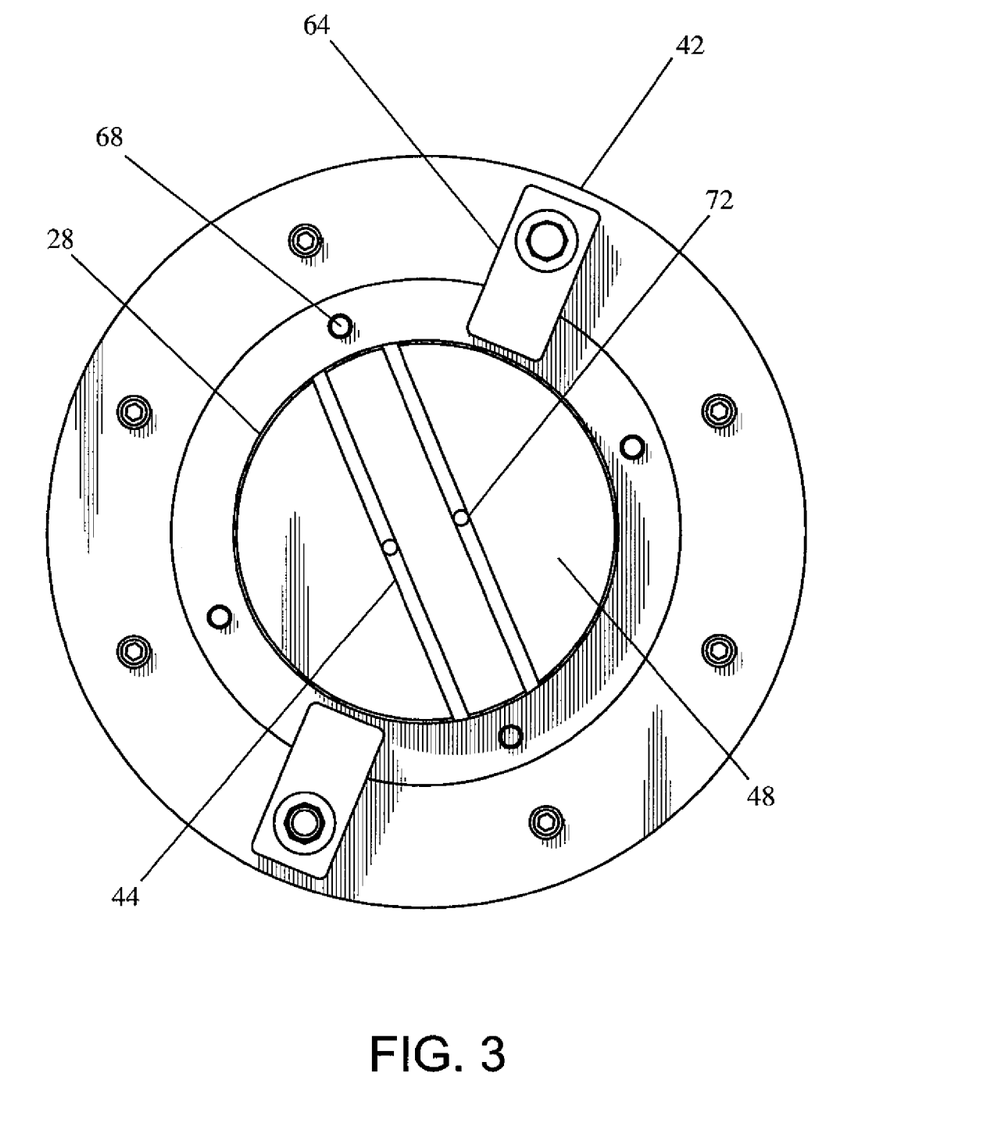
FIG. 3 is a bottom plan view of a rubber polishing disc clamped to a metal plate.

As shown in FIG. 3, mounting plate 42 carries the disc 28 via clamps 64 which are carried by the mounting plate 42 via bolts 62. Clamps 64 can be rotated in order to allow the disc 28 to be placed in the desired location. Pins 66 (FIG. 4) allow the disc 28 to be placed in a consistent location by aligning the pin holes 68 in the disc 28 with the pins 66. Once pins 66 are aligned with pin holes 68 and inserted therein, the disc 28 is prevented from rotating except when the entire shaft assembly 12 rotates. Then clamps 64 can be rotated to the FIG. 3 position in order to secure disc 28 to mounting plate 42. Thus, pins 66 and clamps 64 allow for easy and accurate installation of the disc 28.

Figure 4:
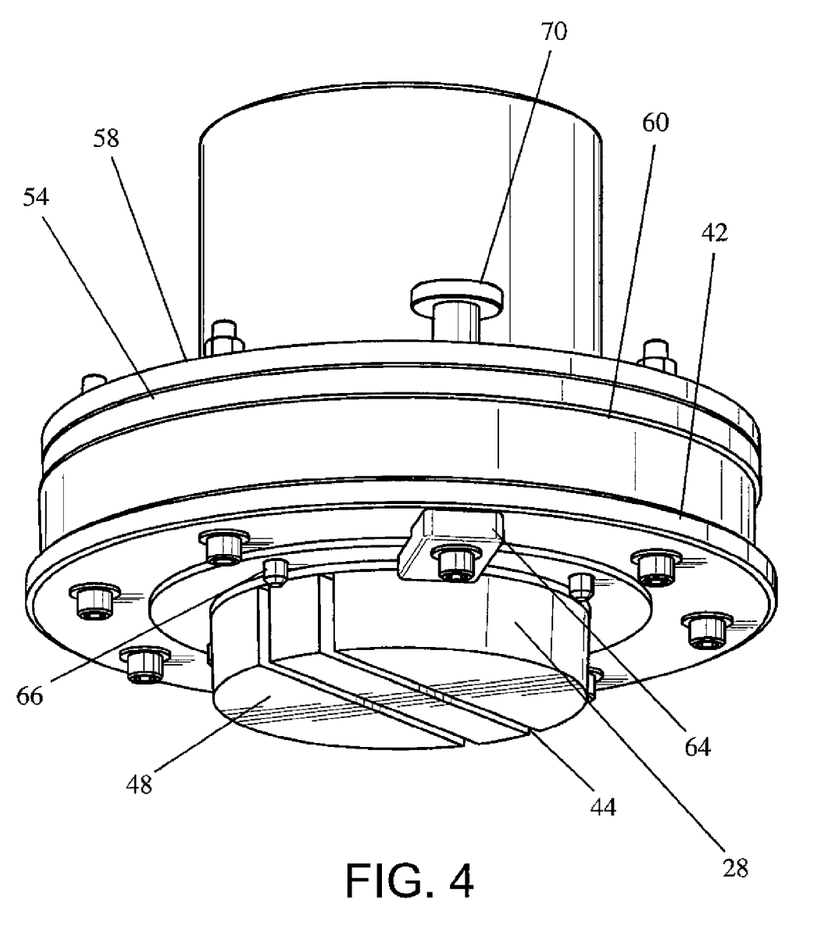
FIG. 4 is a perspective view of the rubber disc clamped to a mounting plate.

For additional ease of securement of a disc 28 in a desired location, a knob 70 may be coupled to bolt 62 to facilitate the tightening and loosening of the bolt 62. When bolt 62 contains threaded ends, the manipulation of knob 70 allows for tightening and loosening of the coupling created by bolt 62. Thus, manipulating the knob 70 such that the coupling created by bolt 62 is tightened assists in securing the disc 28 in a desired location.

Once disc 28 is secured in a desired location, it can be lowered in order to contact a sample 74. As discussed above, the disc 28 includes an upper surface 46 containing at least one aperture 72 therein, and an opposed lower surface 48 containing at least one slot 44 in the first surface. The aperture 72 communicates with the slot 44 such that water flowing to disc 28 can flow through the disc 28 by flowing through an aperture 72, through a slot 44, and to a top surface of sample 74.

As best shown in FIG. 3, the apertures 72 can be located near the center of disc 28. The water flowing from the apertures 72 and through the slots 44 is intended to lubricate a surface of a sample 74 and to flush residue off sample 74 as it is being prepared for testing by machine 10. Disc 28 preferably includes two substantially parallel slots 44 which help to remove, or squeegee, residue (such as asphalt or rubber debris) off of sample 74 and distribute the water evenly across a surface of sample 74. This design can further aid in the removal of residue in addition to allowing for identical polishing action in either rotational direction. This design also offers improved polishing over other feasible designs. Water is thus distributed to an interface between disc 28 and sample 74.

Disc 28 is made from a material that is able to manipulate the sample 74 in a desired manner. In a particular embodiment, disc 28 is made from a hard rubber composition. In a particular embodiment, disc 28 is made from a hard rubber composition having a Shore A durometer measurement of 90, or approximate thereto.

Sample 74 is particularly envisioned as being an asphalt aggregate material, but machine 10 can be designed to operate with similar sample materials, such as cement, stone, and polymer loaded aggregate material. In particular embodiments, sample 74 is an asphalt aggregate material having properties of wear, traction, and abrasion that match the properties of the naturally occurring raw materials mined from the earth that are used to make the sample.

Figure 6:
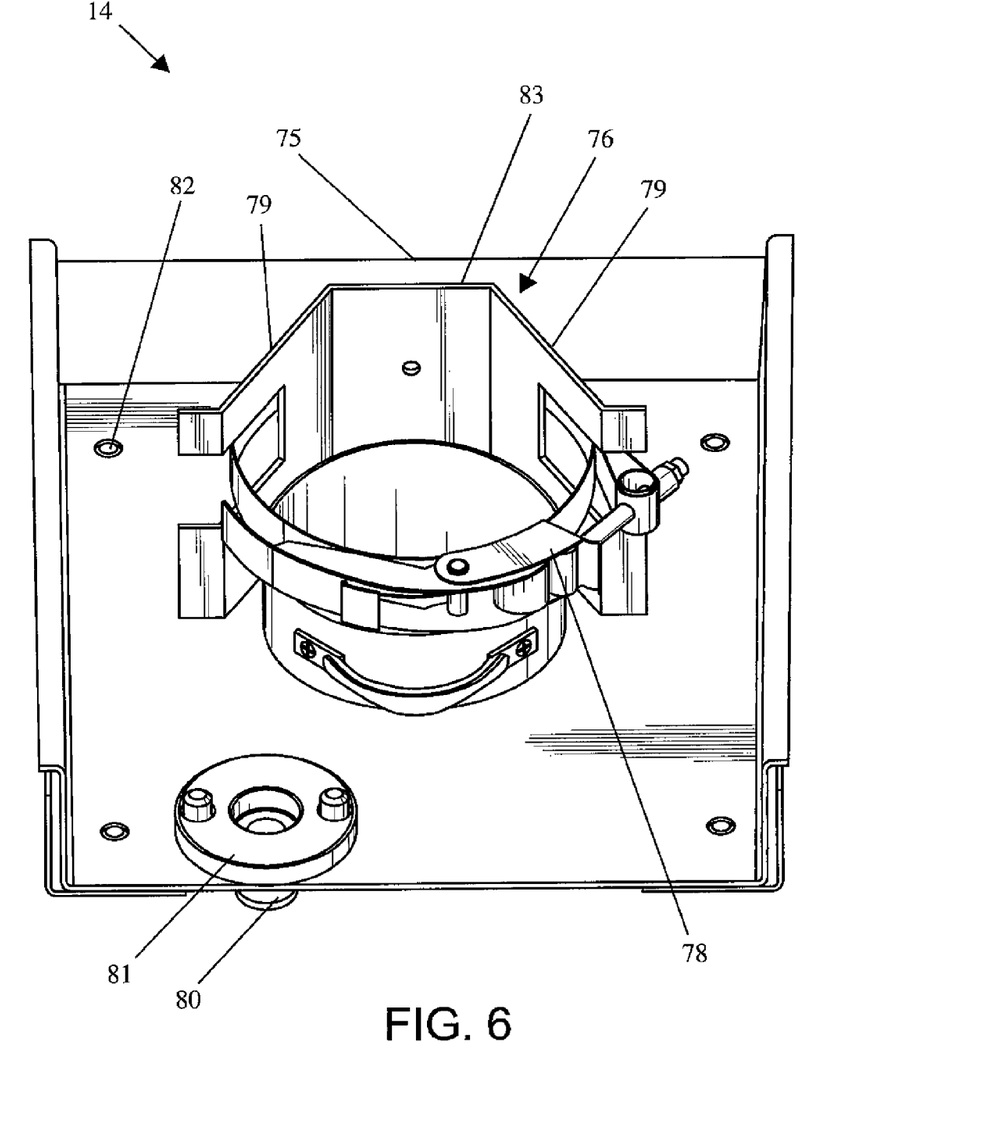
FIG. 6 is a front perspective view of a sample holding assembly.
Figure 7:
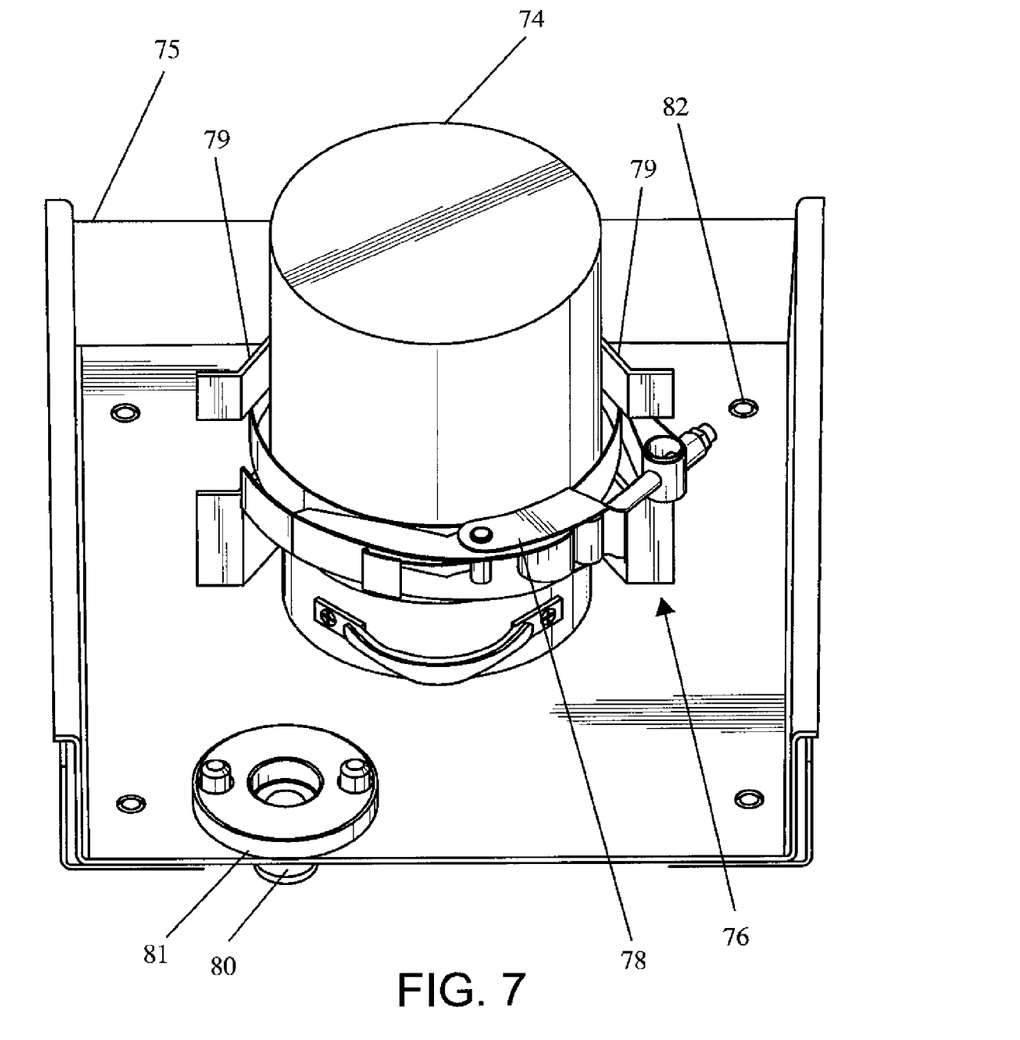
FIG. 7 is a front perspective view of the sample holding assembly shown holding the sample.

Once disc 28 is secured in a desired location, it is lowered in order to contact a sample 74. Sample 74 is carried in a sample assembly 14 which includes a tray 75, a sample holding bracket, generally indicated by the numeral 76, a clamp 78, a water drain 80, and pin holes 82.

Tray 75 is removable from housing 20 for easier cleaning. For positioning the sample assembly 14 in housing 20, pin holes 82 in tray 75 are aligned with pin holes 84 in housing 20. Then, pins (not shown) are inserted through the pin holes 82 and the pin holes 84 in order to position the tray 75 in a desired location. It is also envisioned that a tray 75 could include protrusions from the bottom surface that align with pin holes 84.

Figure 8:
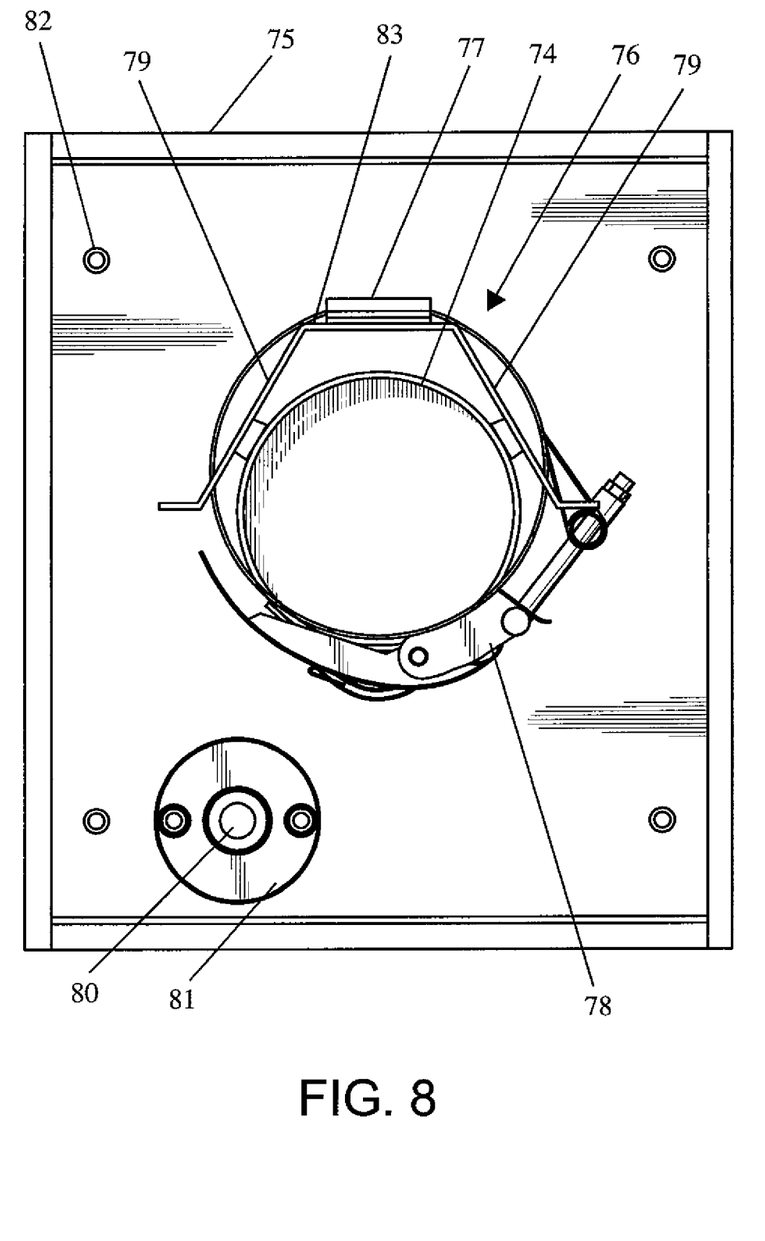
FIG. 8 is a top plan view of a sample holding assembly of FIG. 7.

The sample holding bracket 76 and a clamp 78 are provided in the tray 75 in order to retain a sample 74 in a desired location. Sample holding bracket 76 is designed such that the sample 74 fits therein. Sample holding bracket 76 can be attached to tray 75, as by welding, and includes arms 79 carried by a base 83. Sample 74 is placed inside sample holding bracket 76, and clamp 78 secures sample 74 in a desired location. Clamp 78 can be a T-bolt type clamp and can be held in position by a holder 77. Sample 74 is pressed firmly against sample holding bracket 76 and is held tightly by clamp 78. Arms 79 and base 83 are designed to retain their position, even when sample 74 is held by clamp 78. As such, sample holding bracket 76 and clamp 78 allow for proper placement of sample 74 underneath shaft assembly 12. Particularly, sample holding bracket 76 and clamp 78 are intended to align sample 74 directly underneath disc 28. That is, the central axis of sample 74 is substantially aligned with the central axis of disc 28. Without the proper alignment, the result may be that disc 28 does not come into full and level contact with sample 74.

Sample assembly 14 further includes a water drain 80. The water drain 80 is intended to drain the water that is flowing through channel 26 and through disc 28. Water drain 80 can include a debris trap 81, which acts as a dam for pieces of debris. As water pours off the sample 74 and begins to fill tray 75 with water, debris falls to the bottom of the collected water. When the water reaches a sufficient level, it is able to flow over the top of the debris trap 81 and out of the water drain 80, and further to any attached drain fittings. The debris trap 81 keeps pieces of debris from clogging downstream hoses or drains because the dammed debris can be properly disposed of when the tray 75 is removed from the housing 20.

In order to position the disc 28 to contact the sample 74, a plate assembly 16 is lowered to a lower position. Plate assembly 16 includes a motor plate 86, a motor 88, and at least one coupling 90. Motor 88 carries shaft assembly 12 carrying disc 28. The plate assembly 16 travels downward and upward on one or more guide bars 92.

Plate assembly 16 has a predetermined weight in order to provide a constant force to the sample 74 when the disc 28 contacts the sample 74. Weights (not shown), such as weighted plates, can be positioned on plate 86 to achieve the desired weight for the plate assembly. Based on the constant weight provided by the plate assembly 16, a means for setting the weight, such as a load cell, is not required. In a particular embodiment, the plate assembly 16 preferably has a total weight of approximately 270 pounds.

Motor 88 is coupled to shaft 22 in order to maintain the shaft assembly 14 in a desired position and to rotate the shaft assembly 14. The actuation of the motor 88 enables the shaft assembly 14 to rotate, thereby rotating the disc 28 for manipulating a surface of a sample 74. The rotation speed should be substantially constant in order to achieve consistent results with a speed of approximately 30 rpm being preferred.

Bars 92 guide the plate assembly 16 when moving up and down. Coupling 90, such as a linear bearing assembly, couples the motor plate 86 to the guide bars 92. The plate assembly 16 travels based on the actuation of the actuator assembly 18, now to be described.

Figure 9:
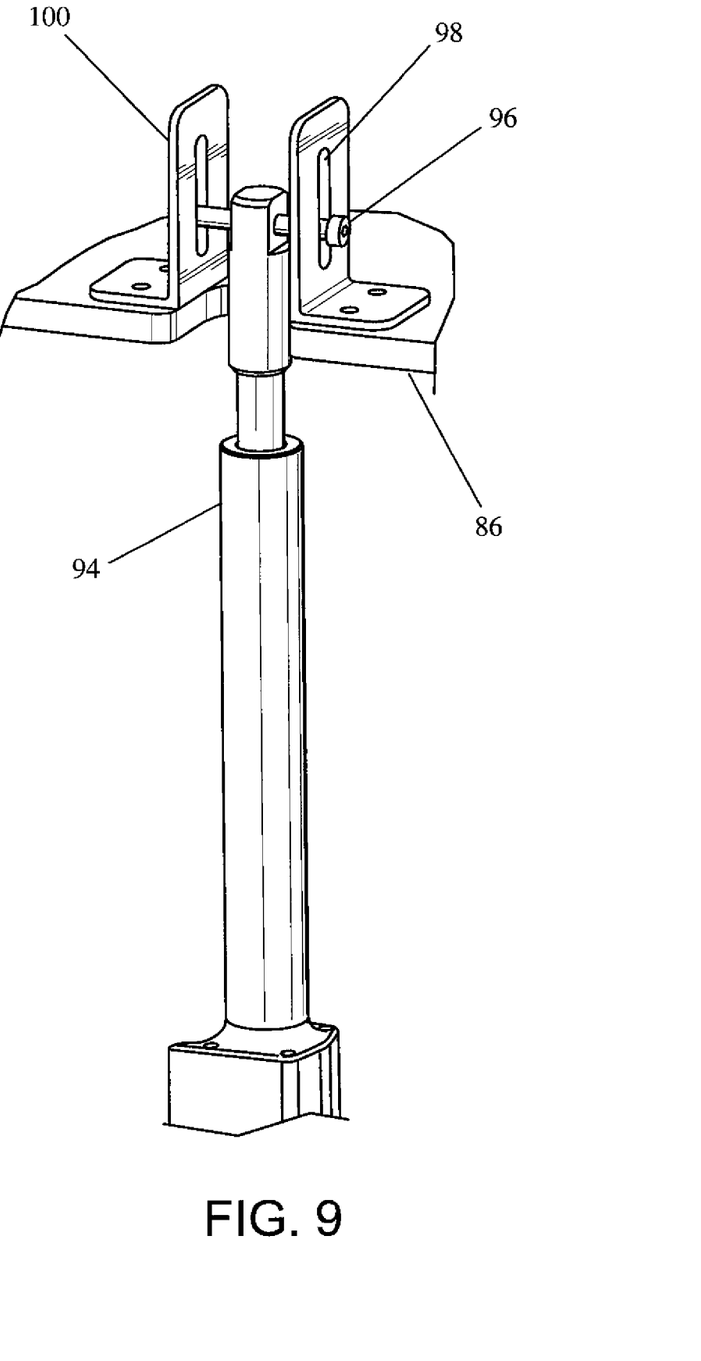
FIG. 9 is a fragmented perspective view of an actuator assembly in a lower position.
Figure 10:
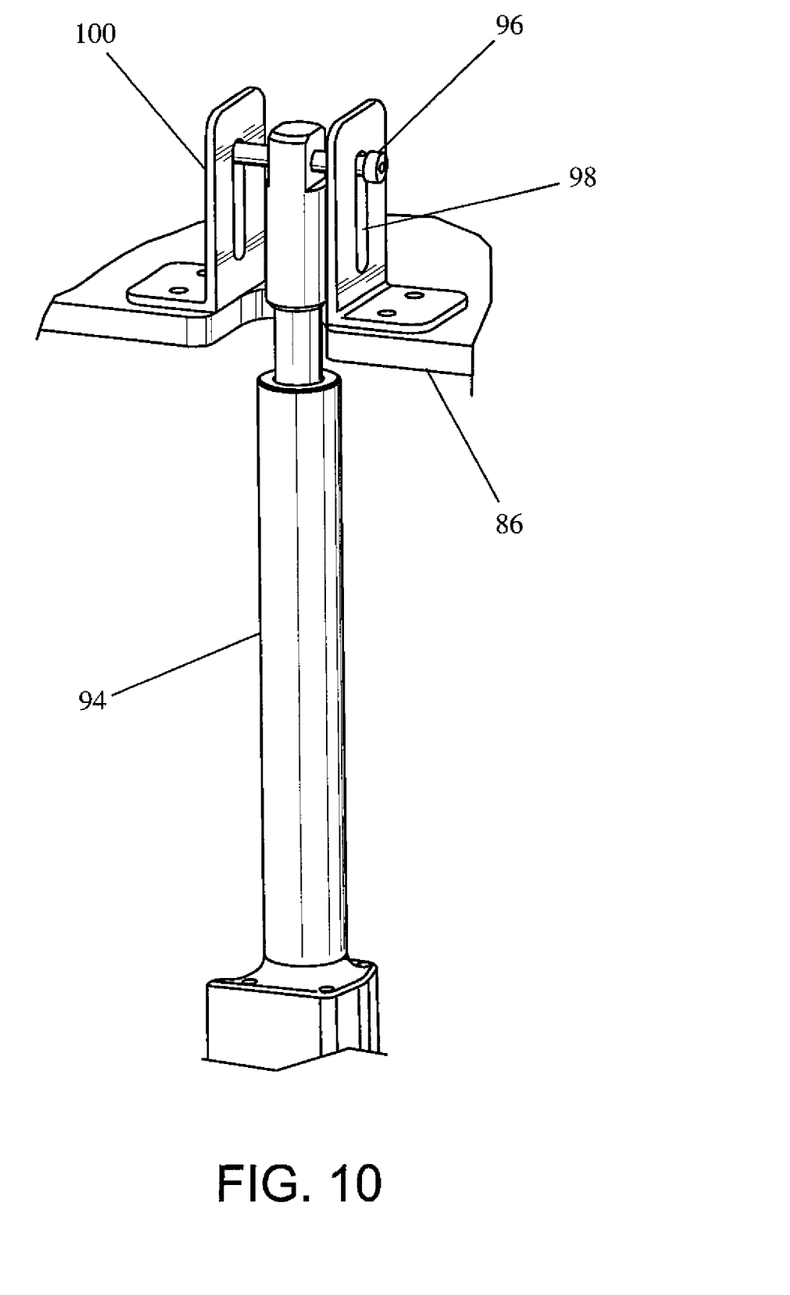
FIG. 10 is a fragmented perspective view of the actuator assembly in a raised position.

In general, actuator assembly 18 causes the plate assembly 16 to move upward, while gravity and deactivation of the actuator assembly 18 cause the plate assembly 16 to move downward. This method of operation allows for constant weight and force to be applied on the sample 74.

In more detail, an actuator 94, such as an electric linear drive system, is actuated to move in an upward direction such that bolt 96 engages the upper end of the guide channels 98 in the angled braces 100 as shown in FIG. 10. The angled braces 100 are coupled to motor plate 86, such that when bolt 96 engages the upper end of guide channels 98 and provides an upward force thereon, the motor plate also moves upwardly. The force of the actuator 94 must be sufficient to overcome the gravitational force of the plate assembly 16 in order to move the plate assembly 16 in an upward direction.

To move the plate assembly 16 downward, the gravitational force of the plate assembly 16 is utilized. The actuator 94 and angled braces 100 do not enact a downward force to the plate assembly 16. This aspect allows the disc 28 to enact a constant force, the gravitational force from the plate assembly 16, to the sample 74. Thus, when the actuator 94 is deactivated, or activated to a force less than that of the gravitational force of the plate assembly 16, the plate assembly 16 travels downward on the guide bars 92. This downward travel continues until the disc 28 engages the sample 74, the position shown in FIG. 9. Once the disc 28 engages the sample 74, the weight of the plate assembly 16 is imparted on the sample 74 and the plate assembly 16 floats on the sample 74. That is, the actuator assembly 18 never pulls down on the plate assembly 16. Instead, the gravitational force simply transfers to the sample 74 for the duration of a polishing process.

Guide channels 98 allows for this floating of the gravitational force on the sample 74. Once the sample 74 is engaged by disc 28, the actuator may continue to go down, in order to move the bolt 96 to a lower position within the guide channels 98, as seen in FIG. 9. But, since plate assembly 16 is held stationary, via disc 28, on top of the sample 74, the weight of the plate assembly 16 is transferred from the bolt 96 and the angled braces 100 to the sample 74 as soon as the sample 74 is engaged by the disc 28. The amount of travel by actuator 94 is designed such that the bolt 96 will never engage with the bottom of guide channels 98, so that the plate assembly 16 is never forcibly pulled down other than by gravitational force. In a particular embodiment, machine 10 is designed such that the actuator is able to be lowered approximately six inches downward, while the plate assembly is only designed to travel approximately four and a half inches downward with a sample 74 in place.

As the disc 28 wears during a polishing process, as it is designed to do, the gravitational force of the plate assembly 16 continues to apply onto the sample, thereby maintaining the constant force on the sample 74. Again, this constant force ensures consistency in the results obtained from the machine 10.

If the plate assembly 16 is travelling downward without a sample 74 in the sample assembly 14, a stopper 102 is provided in order to stop the plate assembly 16 at a certain position of travel. When sample 74 is present, the height of sample 74 is at a higher position than that of stopper 102 such that disc 28 will engage sample 74 before plate assembly 16 contacts stopper 102.

The machine 10 can optionally include a control panel located in a front location of the housing 20. Such a control panel can include a clearly visible timer so that an operator can gauge how much time is left in a process or how much time has passed.

As discussed above, any suitable source of water can be used to provide water through channel 26 and disc 28. The machine 10 can include a water regulator and flow meter for aiding in providing and monitoring a constant flow of water. The water can be roughly adjusted through a regulator, and then finely adjusted through a flow meter. The water flow can be 100 mL/min, or approximate thereto.

Having discussed the structural details of the machine for preparing asphalt samples, the operational steps for operating such a machine will now be discussed in detail. Sample 74 should be properly placed underneath shaft assembly 12. Particularly, sample 74 is aligned directly underneath disc 28, such as by substantially aligning the central axis of sample 74 with the central axis of disc 28.

With the plate assembly 16 held in an upper position, it is then allowed to lower until the disc 28 engages the sample 74, as described above. Prior to lowering plate assembly 16, the water flow can be checked to ensure sufficient flow. After disc 28 engages sample 74, the full water flow is provided and the shaft assembly 12 begins to rotate and is brought to a predetermined rotation speed. This rotation causes disc 28 to manipulate a surface of sample 74, such as by wearing the surface. This wearing of a surface of sample 74 can cause debris of sample 74 to come free from sample 74. This debris is carried by the water flow into tray 75. As discussed above, the water flow begins to fill tray 75 with water and debris falls to the bottom of the collected water. When the water reaches a sufficient level, it is able to flow over the top of the debris trap 81 and out of the water drain 80, and further to any attached drain fittings. The debris trap 81 keeps pieces of debris from clogging downstream hoses or drains because the dammed debris can be properly disposed of when tray 75 is removed from housing 20. It should be appreciated that small pieces of debris may be carried with the water to the water drain 80.

After a predetermined time interval, such as one hour or approximate thereto, the rotation of the shaft assembly 12 is ceased. The machine 10 can have an automated timer to stop the rotation after the predetermined time interval, or a start/stop mechanism for stopping the rotation.

After the rotation is ceased, the shaft assembly 12 and plate assembly 16 are raised to a position so that the sample 74 can be removed from the sample assembly 14 and the disc 28 can be replaced, if necessary. After removing the sample 74, a test may be performed on the sample 74, such as the British Pendulum Test, to determine the effect that the disc 28 has had on the sample 74.

This entire process can then be repeated in order to determine the traction results, wear results, or results of the British Pendulum Test at different stages of usage of the sample material. This process of manipulating a sample material is intended to simulate the anticipated future behavior of this material when used, such as on a roadway. The repetition of this process allows for tracking these results over time, in order to estimate how the material will perform over time. In a particular embodiment, eight increments of the one hour intervals are performed.

It should be appreciated that certain, or all, of the steps in the operational process of use can be automated. This automation can further add to the consistent results that are provided by machine 10. It should also be appreciated that such automation can incorporate delay time periods in order for machine 10 to operate most effectively.

It should be evident that the machine described herein provides an automated process for manipulating a surface of a sample with a constant force for polishing a surface of a sample being provided to the sample. The machine also provides regulated water flow, constant polishing speed, consistent results for the manipulation of a surface of a sample.

In view of the foregoing, it should be apparent that a machine for preparing asphalt samples for testing constructed and operated as described herein accomplishes the objects of the invention and otherwise substantially improves the art.

What is claimed is:

1. An apparatus for preparing a sample asphalt material for testing comprising a rotatable shaft, a disc carried by said rotatable shaft and adapted to engage the sample asphalt material, a sample holding bracket, a plate assembly including a plate, a motor carried by said plate, said motor rotating said rotatable shaft, further comprising an actuator assembly for moving said plate assembly, said actuator assembly including two braces, each brace having a guide channel therein, each guide channel having an upper end, a bolt capable of moving through said guide channels, wherein when upward travel of said plate assembly is desired, said actuator assembly causes said bolt to engage said upper ends of said guide channels, and wherein when downward travel of said plate assembly is desired, said gravitational force of said plate assembly is utilized until said disc engages said sample asphalt material.

2. The apparatus of claim 1, said disc including two substantially parallel slots, each of which do not pass through the center of said disc, each slot including at least one aperture for passing water therethrough.

3. The apparatus of claim 1, further comprising a tray carrying said sample holding bracket, said sample holding bracket being capable of holding the sample asphalt material in a desired position to be engaged by said disc, said tray including a water drain for receiving water passing through said channel.

4. The apparatus of claim 1, further comprising a clamp for securing the sample asphalt material in said sample holding bracket in order to secure said sample asphalt material in a desired position to be engaged by said disc.

5. The apparatus of claim 3, further comprising a housing, said tray having a bottom surface including pins extending therefrom, said housing including pin holes for placing said pins of said tray therein.

6. The apparatus of claim 1, further comprising means to align said disc with the sample asphalt material, thereby enabling said disc to uniformly engage a sample asphalt material having an unleveled surface.

7. An apparatus for maintaining a constant force of a disc on a sample asphalt material which prepares the sample asphalt material for testing comprising a plate assembly for moving the disc and having a desired predetermined weight, said disc being adapted to engage the sample asphalt material, an actuator assembly to move said plate assembly upwardly and to release said plate assembly so that said plate assembly is allowed to move downwardly so that the disc contacts the sample asphalt material with only the weight of said plate assembly thereby being applied to the sample asphalt material, said actuator assembly including two or more angled braces including guide channels respectively therein, each guide channel having an upper end, said actuator assembly further including a bolt capable of travelling through said guide channels, wherein when upward travel of said plate assembly is desired, said actuator assembly causes said bolt to engage said upper ends of said guide channels, and wherein when downward travel of said plate assembly is desired, said gravitational force of said plate assembly is utilized until said disc engages said sample asphalt material.

8. The apparatus of claim 1, said rotatable shaft having a channel formed therein and communicating with a source of water, said disc having a slot therein communicating with water passing through said channel, said disc having a center, wherein said slot does not pass through the center of said disc.

9. The apparatus of claim 1, said sample holding bracket having a base and two arms, a first of said two arms extending from a first side of said base, a second of said two arms extending from a second side of said base, said arms being adapted to engage the sample asphalt material.

* * * * *